(12) United States Patent
Corvera

(10) Patent No.: US 7,767,402 B2
(45) Date of Patent: Aug. 3, 2010

(54) METHODS AND COMPOSITIONS FOR CONTROLLING APPETITE AND MODULATING INSULIN SENSITIVITY

(75) Inventor: Silvia Corvera, Westborough, MA (US)

(73) Assignee: University of Massachusetts, Boston, MA (US)

( * ) Notice: Subject to any disclaimer, the term of this patent is extended or adjusted under 35 U.S.C. 154(b) by 166 days.

(21) Appl. No.: 10/873,364

(22) Filed: Jun. 21, 2004

(65) Prior Publication Data
US 2005/0148494 A1 Jul. 7, 2005

Related U.S. Application Data

(60) Provisional application No. 60/480,264, filed on Jun. 19, 2003.

(51) Int. Cl.
G01N 33/566 (2006.01)
G01N 33/567 (2006.01)
C12N 5/0775 (2010.01)
A61K 38/00 (2006.01)

(52) U.S. Cl. .......................... 435/7.1; 435/7.8; 435/333; 435/334; 435/335; 530/303; 530/304; 536/23.1

(58) Field of Classification Search ................ 514/2; 530/300, 350; 536/23.1; 435/320, 69.1
See application file for complete search history.

(56) References Cited

OTHER PUBLICATIONS

Oyadomari et al. (Aug. 2002) Endoplasmic reticulum stress-mediated apoptosis in pancreatic beta-cells. Apoptosis. vol. 7, No. 4, p. 335-345.*
Oyadomari et al. (2001) Nitric oxide-induced apoptosis in pancreatic beta cells is mediated by the endoplasmic reticulum stress pathway. Proc. Natl. Acad. Sci. U S A. vol. 98, No. 19, pp. 10845-10850.*
Harding et al. (2002) "Endoplasmic reticulum stress and the development of diabetes: a review", Diabetes, vol. 51, pp. S455-S461.*
Bertolotti, et al. (2000) "Dynamic interaction of BiP and ER stress transducers in the unfolded-protein response", Nat. Cell. Biol. vol. 2, No. 6, pp. 326-332.*
WAng et al. (1998) "Cloning of mammalian Ire1 reveals diversity in the ER stress responses", EMBO J., vol. 17, No. 19, pp. 5708-5717.*
Gasic et al. (1999) "Tumor necrosis factor alpha stimulates lipolysis in adipocytes by decreasing Gi protein concentrations", J. Biol. Chem., vol. 274, No. 10, pp. 6670-6675.*
Brackenridge et al. (2006) Contrasting insulin sensitivity of endogenous glucose production rate in subjects with hepatocyte nuclear factor-1beta and -1alpha mutations, Diabetes, vol. 55, No. 2, pp. 405-411.*
Seufert et al. (1998) Differential expression of the insulin gene transcriptional repressor CCAAT/enhancer-binding protein beta and transactivator islet duodenum homeobox-1 in rat pancreatic beta cells during the development of diabetes mellitus, J. Clin. Invest., vol. 101, No. 1, pp. 2528-2539.*
Minami et al. (2000) Insulin secretion and differential gene expression in glucose-responsive and -unresponsive MIN6 sublines, Am. J. Physiol. Endocrinol. Metab., vol. 279, No. 4, pp. E773-E781.*
Calfon M, Zeng H, Urano F, Till JH, Hubbard SR, Harding HP, Clark SG, Ron D. IRE1 couples endoplasmic reticulum load to secretory capacity by processing the XBP-1 mRNA. Nature. Jan. 3, 2002;415(6867):92-6.
Cox JS, Wafter P. A novel mechanism for regulating activity of a transcription factor that controls the unfolded protein response. Cell. Nov. 1, 1996;87(3):391-404.
Foti DM, Welihinda A., Kaufman RJ, Lee AS. Conservation and divergence of the yeast and mammalian unfolded protein response. Activation of specific mammalian endoplasmic reticulum stress element of the grp78/BiP promoter by yeast Hac1. J Biol Chem. Oct. 22, 1999;274(43):30402-9.
Harding HP, Zhang Y, Zeng H, Novoa I, Lu PD, Calfon M, Sadri N, Yun C, Popko B, Paules R, Stojdl DF, Bell JC, Hettmann T, Leiden JM, Ron D. An integrated stress response regulates amino acid metabolism and resistance to oxidative stress. Mol Cell. Mar. 2003;11(3):619-33.
Lee K, Tirasophon W, Shen X, Michalak M, Prywes R, Okada T, Yoshida H, Mori K, Kaufman RJ. IRE1-mediated unconventional mRNA splicing and S2P-mediated ATF6 cleavage merge to regulate XBP1 in signaling the unfolded protein response. Genes Dev. Feb. 15, 2002;16(4):452-66.
Lee AH, Iwakoshi NN, Glimcher LH. XBP-1 regulates a subset of endoplasmic reticulum resident chaperone genes in the unfolded protein response. Mol Cell Biol. Nov. 2003;23(21):7448-59.
Ma Y. Hendershot LM. The unfolding tale of the unfolded protein response. Cell. Dec. 28, 2001;107(7):827-30.
Shen X, Ellis RE, Lee K, Liu CY, Yang K, Solomon A, Yoshida H, Morimoto R, Kurnit DM, Mori K, Kaufman RJ. Complementary signaling pathways regulate the unfolded protein response and are required for C. elegans development. Cell. Dec. 28, 2001;107(7):893-903.
Urano F, Bertalotti A, Ron D. IRE1 and efferent signaling from the endoplasmic reticulum. J Cell Sci. Nov. 2000;113 Pt 21:3697-702.
Urano F, Calfon M, Yoneda T, Yun C, Kiraly M, Clark SG, Ron D. A survival pathway for Caenorhabditis elegans with a blocked unfolded protein response. J Cell Biol. Aug. 19, 2002;158(4):639-46.

* cited by examiner

Primary Examiner—Anand U Desai
Assistant Examiner—Samuel Liu
(74) Attorney, Agent, or Firm—Lahive & Cockfield, LLP; Debra J. Milasincic, Esq.; Richard B. Emmons

(57) ABSTRACT

The invention features methods of enhancing whole body insulin sensitivity by modulating the endoplasmic reticulum (ER) stress response pathway in adipose cells. In one aspect, the methods involve targeting chaperone proteins important in the ER stress response pathway, for example, BiP and ERO-1. Another aspect features targeting the upstream transcription factors (e.g., CHOP-1 and XBP-1) of the genes encoding the chaperone proteins (and/or other ER proteins). Screening assays for identification of modulators of these ER proteins and/or transcription factors are also featured.

10 Claims, No Drawings

METHODS AND COMPOSITIONS FOR CONTROLLING APPETITE AND MODULATING INSULIN SENSITIVITY

RELATED APPLICATIONS

This application claims the benefit of U.S. Provisional Application No. 60/480,264, filed Jun. 19, 2003, entitled "Methods and Compositions for Controlling Appetite and Modulating Insulin Sensitivity", the entire contents of which are incorporated herein by this reference.

BACKGROUND OF THE INVENTION

Diabetes is a chronic metabolic disorder which afflicts 16 million people in the United States, over one and one half million of whom have its most severe form, childhood diabetes (also referred to as juvenile, type 1 or insulin-dependent diabetes). Insulin-dependent diabetes appears suddenly, most often in children and young adults, and progresses rapidly. In this form, the pancreas ceases to manufacture insulin, a hormone necessary to convert the food we eat into energy for the body. Adult onset diabetes (also referred to as late-onset, type 2 or non-insulin-dependent diabetes) develops especially in adults, and most often in obese individuals, and is characterized by hyperglycemia resulting from impaired insulin utilization coupled with the body's inability to compensate with increased insulin.

In the United States, diabetes is the fourth leading cause of death, killing more than 162,000 people each year. Notably, the mortality rate of patients with insulin-dependent diabetes increases dramatically after 15 years of disease duration. In addition, virtually every major organ system in the body is damaged by diabetes. Complications can include blindness, kidney failure, heart disease, stroke, amputation of extremities, loss of nerve sensation, early loss of teeth, high-risk pregnancies and babies born with birth defects.

Currently, insulin injection is the only treatment method available for the over 1.5 million type 1 diabetics and becomes the eventual course of treatment for many of the more than 16 million type 2 diabetics in the United States. Nutritional therapies that positively impact glucose uptake in the face of insulin insufficiency (e.g., increase insulin sensitivity) would have a major impact on the long term treatment costs associated with diabetic care.

More than half of U.S. adults are overweight and nearly one-quarter of the U.S. adults are considered to be obese. The increasing prevalence of overweight and obesity is a major public health concern, since obesity is associated with several chronic diseases. For example, overweight and obesity are known risk factors for diabetes, heart disease, stroke, hypertension, gallbladder disease, osteoarthritis, sleep apnea, and some forms of cancer such as uterine, breast, colorectal, kidney, and gallbladder. Furthermore, obesity is associated with high cholesterol, complications of pregnancy, menstrual irregularities, hirsutism, and increased surgical risk.

Pharmacological treatments for disorders caused by or exacerbated by improper glucose uptake are needed. Specifically, compositions for the treatment of diabetes and obesity would be a great boon to subjects suffering from these disease states.

SUMMARY OF THE INVENTION

The present invention features methods of enhancing whole body insulin sensitivity by modulating the endoplasmic reticulum (ER) stress response pathway in adipose cells. In one aspect, the methods involve targeting chaperone proteins important in the ER stress response pathway, for example, immunoglobulin heavy chain binding protein (BiP) and endoplasmic reticulum oxidoreductin 1 (ERO-1). Another aspect features targeting the upstream transcription factors (e.g., X box binding protein-1 (XBP-1) or CCAAT/ enhancer binding protein homologous protein (CHOP) of the genes encoding the chaperone proteins (and/or other ER proteins). Screening assays for identification of modulators of these ER proteins and/or transcription factors are also featured.

Other features and advantages of the invention will be apparent from the following detailed description and claims.

DETAILED DESCRIPTION OF THE INVENTION

The adipose cell (e.g., adipocyte) has been shown to synthesize and secrete factors that control appetite and insulin sensitivity. These factors must be correctly processed by the endoplasmic reticulum of the adipose cell to be secreted. The present invention is based, at least in part on the discovery that the differentiation of adipocytes from their precursor cells (preadipocytes) involves molecules associated with the endoplasmic reticulum stress response pathway. More specifically, differentiation of adipocytes is associated with the increased expression of endoplasmic reticulum stress response pathway molecule, e.g., endoplasmic reticulum chaperones, required for protein processing. These include the proteins BiP and ERO-1. It has also been discovered that an induction of transcription factors necessary for transcription of chaperones and other endoplasmic reticulum proteins may be necessary for the expansion of endoplasmic reticulum function seen during adipogenesis. These include the transcription factors CHOP-1 and XBP-1. The proper expression and/or activity of these chaperone and transcription factor molecules in turn ensures appropriate adipocyte production and response to insulin, e.g., increased glucose uptake and appetite control.

Accordingly, the present invention features modulation of the components of the endoplasmic reticulum stress response pathway, including but not limited to, BiP, ERO1, XBP-1 and CHOP1, to achieve amelioration of insulin resistance (or enhanced insulin sensitivity) in a subject in need thereof, for example, in a subject having type 2 diabetes. Based, at least in part, on the discovery that elements of the endoplasmic reticulum stress response pathway are activated in a fat cell upon adipogenesis, the invention also features screening assays to identify test compounds that modulate the expression and/or activity of such elements. Because these elements are likely to be crucial for the function of the adipocyte as an endocrine cell, the invention further features using, targeting and/or modulating these elements for the purpose of controlling whole body metabolism, e.g., appetite and/or insulin sensitivity.

So that the invention may be more readily understood, certain terms are first defined.

As used herein, the term "cellular differentiation" includes the process by which the developmental potential of cells is restricted and they acquire specific developmental fates. Differentiated cells are recognizably different from other cell types.

The term "insulin" refers to a polypeptide hormone (molecular weight of approximately 5700) naturally produced by the pancreas (secreted by beta cells in the islets of Langerhans of the pancreas) of a mammal which controls the amounts of glucose present in the blood by stimulating the uptake of glucose by muscle and adipose tissue.

The term "insulin sensitivity" refers to the capacity of a cell, for example, a muscle cell (e.g., skeletal muscle cell) or fat cell (e.g., an adipocyte), or organism to sense or respond to stimulation by insulin or to insulin signaling. The preferred response to insulin or insulin signaling is glucose uptake.

The term "insulin resistance" (or "insulin insensitivity") refers to a condition or disorder in which the tissues of the body fail to respond normally to insulin. Insulin resistance manifests itself in pathologically elevated endogenous insulin and glucose levels and predisposes a mammal to the development of a cluster of abnormalities, including some degree of impaired glucose tolerance, an increase in plasma triglycerides and low density lipoprotein cholesterol (LDL) levels, a decrease in high-density lipoprotein cholesterol (HDL) levels, high blood pressure, hyperuricemia, a decrease in plasma fibrinolytic activity, an increase in cardiovascular disease and atherosclerosis. Reaven, G. M. Physiol-Rev. 75(3): 473-86 (1995). Decompensated insulin resistance is widely believed to be an underlying cause of non-insulin dependent diabetes mellitus.

The term "preadipocyte" refers to a cell existing in or isolated from fat tissue which is capable of replicating yet is committed to the adipogenic phenotype (i.e., is committed to differentiate into an adipocyte or fat cell). In their undifferentiated state, cultured preadipocytes resemble fibroblasts (i.e., have a fibroblast-like morphology). In particular, they exhibit a flattened, adherent morphology and contain very little microscopically-detectable lipid.

The term "adipocyte" refers to a cell existing in or derived from fat tissue which is terminally differentiated. In their differentiated state, adipocytes assume a rounded morphology associated with cytoskeletal changes and loss of mobility. They further accumulate lipid as multiple small vesicles that later coalesce into a single, large lipid droplet displacing the nucleus.

The term "leptin" refers to a peptide hormone that is produced by fat cells and plays a role in body weight regulation by acting on the hypothalamus to suppress appetite and burn fat stored in adipose tissue.

The term "endoplasmic reticulum" refers to a system of interconnected vesicular and lamellar cytoplasmic membranes that functions especially in the transport of materials within the cell and that is studded with ribosomes.

Various methodologies of the instant invention include steps that involve comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing a methodology, as described herein. For example, a transcription rate, mRNA level, translation rate, protein level, biological activity, cellular characteristic or property, genotype, phenotype, etc. can be determined prior to performing a methodology, as described herein. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an endoplasmic reticulum stress response pathway molecule modulator that may occur naturally in a subject (i.e., exposure that may occur as a result of a natural physiological process).

As used herein, the term "test compound" refers to a compound that has not previously been identified as, or recognized to be, a modulator of the activity being tested. The term "library of test compounds" refers to a panel comprising a multiplicity of test compounds.

As used herein, the term "dominant negative endoplasmic reticulum stress response pathway molecule protein" includes endoplasmic reticulum stress response pathway molecules (e.g., portions or variants thereof) that compete with native (i.e., naturally occurring wild-type endoplasmic reticulum stress response pathway molecules, but which do not have endoplasmic reticulum stress response pathway molecule activity. Such molecules effectively decrease endoplasmic reticulum stress response pathway molecule activity in a cell. As used herein, "dominant negative endoplasmic reticulum stress response pathway molecule protein" refers to a modified form of an endoplasmic reticulum stress response pathway molecule which is a potent inhibitor of endoplasmic reticulum stress response pathway molecule activity.

As used herein, the term "indicator composition" refers to a composition that includes a protein of interest (e.g., an endoplasmic reticulum stress response pathway molecule or a molecule in a signal transduction pathway involving endoplasmic reticulum stress response pathway molecules), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. In a preferred embodiment, a cell of the invention is a murine or human cell.

As used herein, the term "engineered" (as in an engineered cell) refers to a cell into which a nucleic acid molecule e.g., encoding an endoplasmic reticulum stress response pathway molecule protein has been introduced.

As used herein, the term "cell free composition" refers to an isolated composition, which does not contain intact cells. Examples of cell free compositions include cell extracts and compositions containing isolated proteins.

As used herein, the term "reporter gene" refers to any gene that expresses a detectable gene product, e.g., RNA or protein. Preferred reporter genes are those that are readily detectable. The reporter gene can also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7: 725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368) and green fluorescent protein (U.S. Pat. No. 5,491,084; WO 96/23898).

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282: 63), and natural product extract libraries. In another embodiment, the compounds are small, organic non-peptidic compounds. In a further embodiment, a small molecule is not biosynthetic. For example, a small molecule is preferably not itself the product of transcription or translation.

Various aspects of the invention are described in further detail in the following subsections:

Appetite Control

In one aspect of the present invention, methods are featured to modulate obesity, e.g., adipocyte development, by modulating the endoplasmic reticulum stress response pathway by modulating the expression and/or activity of at least one of the endoplasmic reticulum stress response pathway molecules described herein. Preferred chaperone proteins include, but are not limited to, BiP and ERO-1. Preferred transcription factors include, but are not limited to, X box binding protein-1 (XBP-1) and CCAAT/enhancer binding protein homologous protein (CHOP) (e.g., CHOP-1).

Appetite control is dependent on the peripheral physiology and metabolic interations in the brain. Upon consumption of a meal an cascade of enzymes are released which communicate with the central nervous system and in turn control the termination of the food intake.

Certain short-term hormonal and neural signals derive from the gastrointestinal tract, such as cholecystokinin and ghrelin. Other hormones derive from the pancreas, such as insulin, or from adipose cells, such as leptin. Together with circulating nutrients, these signals act at several central nervous system (CNS) sites but the pathways converge on the hypothalamus, which contains a large number of peptide and other neurotransmitters that influence food intake. When energy stores are low, production of leptin from adipose tissue, and thus circulating leptin concentrations fall, leading to increased production of hypothalamic neurotransmitters that strongly increase food intake, such as neuropeptide Y (NPY), galanin and agouti-related protein (AGRP) and decreased levels of alpha-melanocyte-stimulating hormone (alpha-MSH), cocaine and amphetamine-regulated transcript (CART) and neurotensin that reduce food intake and increase energy expenditure. Leptin, which is synthesized and secreted from fat tissues, acts on several neuronal subtypes within the arcuate nucleus, which inhibits the production of neuropeptide-Y (NPY) and AGRP peptide and galanin; it stimulates production of POMC, CART, and neurotensin. The finding that mutations in leptin and POMC lead to severe early onset obesity in humans has highlighted the importance of these peptides in humans.

The Endoplasmic Reticulum Stress Response Pathway

The endoplasmic reticulum (ER) is an organelle specialized for protein folding and assembly of membrane proteins and of proteins destined for trafficking to lysosomes and the extracellular space. Newly synthesized lysosomal, secretory, and membrane proteins are translocated into the lumen of the ER that provides an oxidizing environment and contains a multitude of ER resident proteins that facilitate the folding.

Accordingly, in another aspect, the instant invention features modulation of the endoplasmic reticulum stress response pathway comprising modulating the expression and/or activity of at least one of the endoplasmic reticulum stress response pathway molecules, e.g., endoplasmic reticulum chaperones or other factors which control transcription of the genes encoding said chaperones, e.g., transcription factors. As used herein, an "endoplasmic reticulum stress response pathway molecule" includes but is not limited to chaperone proteins and transcription factors associated with said chaperones that respond to endoplasmic reticulum stress. These molecules are upregulated or downregulated in response to ER stress, due to for example, preadipocyte differentiation. Exemplary endoplasmic reticulum stress response pathway molecules include, but are not limited to ER chaperone proteins and associated transcription factors. Preferred chaperone proteins include, but are not limited to, BiP and ERO-1. Preferred transcription factors include, but are not limited to, X box binding protein-1 (XBP-1) and CCAAT/enhancer binding protein homologous protein (CHOP) (e.g., CHOP-1). As such transcription factors are important in regulating expression of the genes encoding said chaperones (or other endoplasmic reticulum proteins), transcription-based assays featuring these factors are suitable for use, for example, in the screening assays described herein.

As used herein, the term "endoplasmic reticulum (ER) stress" includes conditions such as for example, the differentiation of preadipocytes into adipocytes. ER stress also includes conditions such as the presence of reducing agents, depletion of ER lumenal $Ca^{2+}$, inhibition of glycosylation or interference with the secretory pathway (by preventing transfer to the Golgi system), which lead to an accumulation of misfolded protein intermediates and increase the demand on the chaperoning capacity, and induce ER-specific stress response pathways. ER stress pathways involved with protein processing include the Unfolded Protein Response (UPR) and the Endoplasmic Reticulum Overload Response (EOR) which is triggered by certain of the same conditions known to activate UPR, as well as by heavy overexpression of proteins within the ER, due to, for example, the differentiation of preadipocytes into adipocytes.

The transcription of many of the genes encoding ER resident proteins, such as BiP (immunoglobulin binding protein or glucose-regulated protein 78 "GRP78" or heat shock 70 kDa protein 5; GI:16507237), is upregulated in response to glucose deprivation, in response to conditions that disrupt protein folding in the ER, and in response to the presence of unfolded or unassembled proteins in the ER. Thus, an unfolded protein response (UPR) exists in cells that detect unfolded protein in the ER lumen to transduce a signal(s) across the ER membrane to activate transcription of selective genes in the nucleus.

Protein folding is facilitated by the presence of a vast array of molecular chaperones and enzymes. For many secretory proteins, the acquisition of the native structure requires the formation of intra- and inter-molecular disulfide bonds. This process generally takes place in the endoplasmic reticulum (ER). This organelle contains many oxidoreductases, belonging to the protein disulfide isomerase family, which share a characteristic CXXC motif. These enzymes are thought to catalyze the formation of native disulfides in cargo proteins. Exemplary enzymes include members of the Endoplasmic Reticulum Oxidoreductin 1 (ERO1) family (e.g., ERO1-like or ERO-1L; GI:7657069; and ERO-1Lbeta; GI:31377735). Members of this family are required for the formation of disulphide bonds in the ER. As used herein, the term "protein folding or transport" encompasses posttranslational processes including folding, glycosylation, subunit assembly and transfer to the Golgi compartment of nascent polypeptide chains entering the secretory pathway, as well as extracytosolic portions of proteins destined for the external or internal cell membranes, that take place in the ER lumen. Proteins in the ER are destined to be secreted or expressed on the surface of a cell. Accordingly, expression of a protein on the cell surface or secretion of a protein can be used as indicators of protein folding or transport.

As referred to herein, the term "proteasome pathway" refers to a pathway by which a variety of cellular proteins are degraded and is also called the ubiquitin-proteasome pathway. Many proteins are marked for degradation in this pathway by covalent attachment of ubiquitin.

As such, endoplasmic reticulum chaperone proteins and associated transcription factors are important in regulating expression of the genes encoding said chaperones (or other endoplasmic reticulum proteins), and therefore, transcription-based assays featuring these factors are suitable for use, for example, in the screening assays described herein.

Screening Assays

The methods of the invention are also suitable for use in methods to identify and/or characterize potential pharmacological agents, e.g. identifying new pharmacological agents from a collection of test substances and/or characterizing mechanisms of action and/or side effects of known pharmacological agents. Cell-free as well as cell-based assays are contemplated. In the cell-based assays of the invention, at least one component important or crucial to the function of the adipocyte as an endocrine cell (e.g., BiP, ERO1, XBP-1 and/or CHOP1) is assayed in vitro in the presence of a test compound and the ability of the test compound to bind to or modulate the activity of the component is determined. An effect on the component is an indicator of the pharmacological potential of the compound. Expression of endoplasmic reticulum stress response pathway molecules (e.g., chaperones or enzymes) can be assayed. Endoplasmic reticulum stress response pathway molecules (e.g., chaperones or enzymes) can be assayed for expression and/or any biochemical activity characteristic of said component. Transcription factor expression can be assayed. Transcription factor activity (i.e., the ability to regulate or control transcription of an endoplasmic reticulum stress response pathway protein) can be assayed. Transcription-based assays (e.g., featuring a reporter gene readout) are exemplary. Cell-based assays preferably feature cells expressing at least one endoplasmic reticulum protein (e.g., a chaperone or enzyme), cells expressing at least one endoplasmic reticulum stress response pathway protein (e.g., a chaperone or enzyme) and at least a transcription factor which regulates transcription of said protein, or a complement of said transcription factors and proteins.

As used herein, the various forms of the term "modulate" include stimulation (e.g., increasing or upregulating a particular response or activity) and inhibition (e.g., decreasing or downregulating a particular response or activity).

As used herein, the term "a modulator of an endoplasmic reticulum stress response pathway molecule" includes a modulator of endoplasmic reticulum stress response pathway molecule expression, processing, post-translational modification, and/or activity. The term includes agents, for example a compound or compounds which modulate transcription of an endoplasmic reticulum stress response pathway molecule gene, processing of an endoplasmic reticulum stress response pathway molecule mRNA (e.g., splicing), translation of an endoplasmic reticulum stress response pathway molecule mRNA, post-translational modification of an endoplasmic reticulum stress response pathway molecule protein (e.g., glycosylation, ubiquitination) or activity of an endoplasmic reticulum stress response pathway molecule protein. A "modulator of endoplasmic reticulum stress response pathway molecule activity" includes compounds that directly or indirectly modulate endoplasmic reticulum stress response pathway molecule activity. For example, an indirect modulator of endoplasmic reticulum stress response pathway molecule activity can modulate a non-endoplasmic reticulum stress response pathway molecule which is in a signal transduction pathway that includes an endoplasmic reticulum stress response pathway molecule. Examples of modulators that directly modulate endoplasmic reticulum stress response pathway molecule expression, processing, post-translational modification, and/or activity include antisense or siRNA nucleic acid molecules that bind to endoplasmic reticulum stress response pathway molecule mRNA or genomic DNA, intracellular antibodies that bind to an endoplasmic reticulum stress response pathway molecule intracellularly and modulate (i.e., inhibit) endoplasmic reticulum stress response pathway molecule activity, activating antibodies that bind to an endoplasmic reticulum stress response pathway molecule and modulate (i.e., enhance) endoplasmic reticulum stress response pathway molecule activity, endoplasmic reticulum stress response pathway molecule peptides that modulate (inhibit or enhance) the interaction of endoplasmic reticulum stress response pathway molecule with a target molecule, and expression vectors encoding endoplasmic reticulum stress response pathway molecule that allow for increased expression of endoplasmic reticulum stress response pathway molecule activity in a cell, dominant negative forms of endoplasmic reticulum stress response pathway molecule, as well as chemical compounds that act to specifically modulate the activity of endoplasmic reticulum stress response pathway molecule.

As used interchangeably herein, the terms "endoplasmic reticulum stress response pathway molecule activity," "biological activity of endoplasmic reticulum stress response pathway molecule" or "functional activity of endoplasmic reticulum stress response pathway molecule," include activities exerted by an endoplasmic reticulum stress response pathway molecule protein on an endoplasmic reticulum stress response pathway molecule responsive cell or tissue, e.g., a preadipocyte or adipocyte, or on an endoplasmic reticulum stress response pathway molecule nucleic acid molecule or protein target molecule, as determined in vivo, or in vitro, according to standard techniques. Endoplasmic reticulum stress response pathway molecule activity can be a direct activity, such as an association with an endoplasmic reticulum stress response pathway molecule-target molecule. Alternatively, an endoplasmic reticulum stress response pathway molecule activity is an indirect activity, such as a downstream biological event mediated by interaction of the endoplasmic reticulum stress response pathway molecule protein with an endoplasmic reticulum stress response pathway molecule target molecule. The biological activities of endoplasmic reticulum stress response pathway molecules are described herein and include: e.g., modulation of the endoplasmic reticulum stress response, modulation of the UPR, modulation of cellular differentiation, modulation of the adipocyte differentiation, modulation of the proteasome pathway, modulation of protein folding and transport, glucose uptake, insulin secretion. These findings provide for the use of endoplasmic reticulum stress response pathway molecules for as drug targets and as targets for modulation of these biological activities in cells and for therapeutic intervention in diseases such as obesity and those associated with insulin sensitivity aberrations, e.g., Type II diabetes.

Cell Free Assays

In one embodiment, an assay of the present invention is a cell-free assay in which an endoplasmic reticulum stress response pathway molecule (or biologically active portion thereof) is contacted with a test compound and the ability of the test compound to bind to the endoplasmic reticulum stress response pathway molecule polypeptide (or bioactive fragment thereof) is determined. Binding of the test compound to the endoplasmic reticulum stress response pathway molecule polypeptide (or bioactive fragment thereof) can be accomplished, for example, by coupling the test compound or the endoplasmic reticulum stress response pathway molecule polypeptide (or bioactive fragment thereof) with a radioisotope or enzymatic label such that binding of the test compound to the endoplasmic reticulum stress response pathway molecule polypeptide (or bioactive fragment thereof) can be determined by detecting the labeled compound or polypeptide in a complex. For example, test compounds or polypeptides can be labeled with $^{125}I$, $^{35}S$, $^{14}C$, or $^{3}H$, either directly or indirectly, and the radioisotope detected by direct counting of radioemmission or by scintillation counting. Alternatively, test compounds or polypeptides can be enzymatically labeled with, for example, horseradish peroxidase, alkaline phosphatase, or luciferase, and the enzymatic label detected by determination of conversion of an appropriate substrate to product.

Binding of the test compound to the endoplasmic reticulum stress response pathway molecule polypeptide (or bioactive fragment thereof) can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon of surface plasmon resonance (SPR) can be used as an indication of real-time reactions between biological molecules.

In a preferred embodiment, the assay includes contacting the endoplasmic reticulum stress response pathway molecule polypeptide (or biologically active portion thereof) with a endoplasmic reticulum stress response pathway molecule target molecule (or a bioactive fragment thereof) to form an assay mixture, contacting the assay mixture with a test compound, and determining the ability of the test compound to interact with the endoplasmic reticulum stress response pathway molecule polypeptide (or bioactive fragment thereof), wherein determining the ability of the test compound to interact with the endoplasmic reticulum stress response pathway molecule polypeptide (or bioactive fragment thereof) comprises determining the ability of the test compound to preferentially bind to the endoplasmic reticulum stress response pathway molecule polypeptide (or the bioactive portion thereof) as compared to the endoplasmic reticulum stress response pathway molecule target molecule. In another embodiment, the assay includes contacting the endoplasmic reticulum stress response pathway molecule polypeptide (or biologically active portion thereof) with a endoplasmic reticulum stress response pathway molecule target molecule (or a bioactive fragment thereof) to form an assay mixture, contacting the assay mixture with a test compound, and determining the ability of the test compound to modulate (e.g., stimulate or inhibit) binding between the endoplasmic reticulum stress response pathway molecule polypeptide and the endoplasmic reticulum stress response pathway molecule target molecule (or a bioactive fragment thereof).

In another embodiment, the assay is a cell-free assay in which an endoplasmic reticulum stress response pathway molecule polypeptide (or bioactive portion thereof) is contacted with a test compound and the ability of the test compound to modulate (e.g., stimulate or inhibit) the activity of the endoplasmic reticulum stress response pathway molecule polypeptide (or biologically active portion thereof) is determined.

In certain embodiments, an endoplasmic reticulum stress response pathway molecule is present within an endoplasmic reticulum membrane preparation or other suitable hydrophilic preparation for maintaining or enhancing the activity of the pathway molecule(s). Determining the ability of the test compound to modulate the activity of an endoplasmic reticulum stress response pathway molecule polypeptide (or bioactive fragment thereof) can be accomplished, for example, by determining the ability of the endoplasmic reticulum stress response pathway molecule polypeptide to modulate the activity of an endoplasmic reticulum stress response pathway molecule binding partner or target molecule by one of the methods described herein for cell-based assays.

In yet another embodiment, the cell-free assay involves contacting an endoplasmic reticulum stress response pathway molecule polypeptide (or biologically active portion thereof) with an endoplasmic reticulum stress response pathway molecule target molecule which binds the endoplasmic reticulum stress response pathway molecule polypeptide to form an assay mixture, contacting the assay mixture with a test compound, and determining the ability of the test compound to preferentially modulate the activity of an endoplasmic reticulum stress response pathway molecule binding partner or target molecule, as compared to the endoplasmic reticulum stress response pathway molecule polypeptide (or biologically active portion thereof).

In more than one embodiment of the above assay methods of the present invention, it may be desirable to immobilize either an endoplasmic reticulum stress response pathway molecule or its binding partner/target molecule to facilitate separation of complexed from uncomplexed forms of one or both of the proteins, as well as to accommodate automation of the assay. Binding of a test compound to an endoplasmic reticulum stress response pathway molecule polypeptide, or interaction of an endoplasmic reticulum stress response pathway molecule polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/endoplasmic reticulum stress response pathway molecule fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or TAP polypeptide, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of endoplasmic reticulum stress response pathway molecule binding or activity determined using standard techniques.

Additional exemplary endoplasmic reticulum stress response pathway molecule fusion proteins include, but are not limited to, chitin binding domain (CBD) fusion proteins, hemagglutinin epitope tagged (HA)-fusion proteins, His fusion proteins (e.g., $His_6$ tagged proteins), FLAG tagged fusion proteins, AU1 tagged proteins, and the like.

Other techniques for immobilizing proteins on matrices can also be used in the screening assays of the invention. For example, either an endoplasmic reticulum stress response pathway molecule polypeptide or an endoplasmic reticulum stress response pathway molecule target molecule can be immobilized utilizing conjugation of biotin and streptavidin. Biotinylated endoplasmic reticulum stress response pathway molecule polypeptide or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with endoplasmic reticulum stress response pathway molecule polypeptide or target molecules but which do not interfere with binding of the endoplasmic reticulum stress response pathway molecule polypeptide to its target molecule can be derivatized to the wells of the plate, and unbound target or endoplasmic reticulum stress response pathway molecule polypeptide trapped in the wells by antibody conjugation. Methods for detecting such complexes, in addition to those described above for the glutathione S-transferase- (GST-) immobilized complexes, include immunodetection of complexes using antibodies reactive with the endoplasmic reticulum stress response pathway molecule polypeptide or target molecule as well as enzyme-linked assays which rely on detecting an enzymatic activity associated with the endoplasmic reticulum stress response pathway molecule polypeptide or target molecule.

In yet another aspect of the invention, the endoplasmic reticulum stress response pathway molecule polypeptides can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with endoplasmic reticulum stress response pathway molecules ("endoplasmic reticulum stress response pathway molecule-binding proteins" or "endoplasmic reticulum stress response pathway molecule-target molecules") and are involved in endoplasmic reticulum stress response pathway molecule activity. Such endoplasmic reticulum stress response pathway molecule-target molecules are also likely to be involved in the regulation of cellular activities modulated by the endoplasmic reticulum stress response pathway molecule polypeptides.

At least one exemplary two-hybrid system is based on the modular nature of most transcription factors, which consist of separable DNA-binding and activation domains. Briefly, the assay utilizes two different DNA constructs. In one construct, the gene that codes for an endoplasmic reticulum stress response pathway molecule polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an endoplasmic reticulum stress response pathway molecule-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the endoplasmic reticulum stress response pathway molecule polypeptide.

Another exemplary two-hybrid system, referred to in the art as the CytoTrap™ system, is based in the modular nature of molecules of the Ras signal transduction cascade. Briefly, the assay features a fusion protein comprising the "bait" protein and Son-of-Sevenless (SOS) and the cDNAs for unidentified proteins (the "prey") in a vector that encodes myristylated target proteins. Expression of an appropriate bait-prey combination results in translocation of SOS to the cell membrane where it activates Ras. Cytoplasmic reconstitution of the Ras signaling pathway allows identification of proteins that interact with the bait protein of interest, for example, endoplasmic reticulum stress response pathway molecule protein. Additional mammalian two hybrid systems are also known in the art and can be utilized to identify endoplasmic reticulum stress response pathway molecule interacting proteins.

Cell Based Assays

In one embodiment, an assay is a cell-based assay in which a cell which expresses an endoplasmic reticulum stress response pathway molecule polypeptide, or biologically active portion thereof, is contacted with a test compound and the ability of the test compound to modulate the activity of the endoplasmic reticulum stress response pathway molecule polypeptide, or biologically active portion thereof, determined. The cell, for example, can be of mammalian origin or a yeast cell. The endoplasmic reticulum stress response pathway molecule polypeptide, for example, can be expressed heterologously or native to the cell. Determining the ability of the test compound to modulate the activity of an endoplasmic reticulum stress response pathway molecule polypeptide, or biologically active portion thereof, can be accomplished by assaying for any of the activities of an endoplasmic reticulum stress response pathway molecule polypeptide described herein.

Determining the ability of the test compound to modulate the activity of an endoplasmic reticulum stress response pathway molecule polypeptide, or biologically active portion thereof, can also be accomplished by assaying for the activity of an endoplasmic reticulum stress response pathway molecule target molecule. In one preferred embodiment, the cell which expresses the endoplasmic reticulum stress response pathway molecule polypeptide, or biologically active portion thereof, further expresses an endoplasmic reticulum stress response pathway molecule target molecule, or biologically active portion thereof.

In another embodiment, an assay is a cell-based assay in which a cell which expresses a endoplasmic reticulum stress response pathway molecule polypeptide, or biologically active portion thereof, is contacted with a bioactive peptide derived from a endoplasmic reticulum stress response pathway molecule target molecule and a test compound and the ability of the test compound to modulate the activity of the endoplasmic reticulum stress response pathway molecule polypeptide, or biologically active portion thereof, determined.

According to the cell-based assays of the present invention, determining the ability of the test compound to modulate the activity of the endoplasmic reticulum stress response pathway molecule polypeptide or biologically active portion thereof, can be determined by assaying for any of the native activities of an endoplasmic reticulum stress response pathway molecule polypeptide described herein, for example, assaying for adipogenesis or glucose uptake. In another embodiment, an assay is a cell-based assay comprising contacting a cell expressing an endoplasmic reticulum stress response pathway molecule and the expression of the endoplasmic reticulum stress response pathway molecule is monitored. Moreover, the activity of the endoplasmic reticulum stress response pathway molecule polypeptide or biologically active portion thereof, can be determined by assaying for an indirect activity which is coincident the activity of an endoplasmic reticulum stress response pathway molecule polypeptide. For example, the effect of the test compound on the ability of an endoplasmic reticulum stress response pathway molecule-expressing cell to uptake glucose in an insulin-dependent manner can be assayed in the presence of the test compound. Furthermore, determining the ability of the test compound to modulate the activity of the endoplasmic reticulum stress response pathway molecule polypeptide or biologically active portion thereof, can be determined by assaying for an activity which is not native to the endoplasmic reticulum stress response pathway molecule polypeptide, but for which the cell has been recombinantly engineered. For example, the cell can be engineered to express an endoplasmic reticulum stress response pathway molecule target molecule which is a recombinant protein comprising a bioactive portion of an endoplasmic reticulum stress response pathway molecule target molecule operatively linked to a non-endoplasmic reticulum stress response pathway molecule target molecule polypeptide. It is also intended that in preferred embodiments, the cell-based assays of the present invention comprise a final step of identifying the compound as a modulator of endoplasmic reticulum stress response pathway molecule activity.

Test Compounds

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In a preferred embodiment, the library is a natural product library, e.g., a library produced by a bacterial, fungal, or yeast culture. In another preferred embodiment, the library is a synthetic compound library.

Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Methods of The Invention

The present invention provides for both prophylactic and therapeutic methods of treating a subject at risk of (or susceptible to) a disorder or having a disorder that would benefit from modulation of the endoplasmic reticulum stress response pathway. Such disorders or diseases include those that are characterized and/or caused by altered insulin sensitivity, for example, weight disorder, for example, obesity, overweight, reduced insulin sensitivity, insulin resistance, diabetes (e.g., Type II diabetes), cachexia, or anorexia. The therapeutic methods a particularly useful for treating obese subjects and/or obese diabetics. The compositions and methods of the invention are also particularly suited for achieving reduction of body fat, improvement of insulin sensitivity, reduction of hyperglycemia, and reduction of hypercholesterolemia.

Desired therapeutic effects include a modulation of any endoplasmic reticulum stress response pathway-associated activity, as described herein. A preferred therapeutic effect is modulation of the expression or activity of the endoplasmic reticulum stress response pathway. Desired therapeutic effects also include an increase in endoplasmic reticulum stress response pathway molecule mRNA expression, endoplasmic reticulum stress response pathway molecule protein levels, or endoplasmic reticulum stress response pathway molecule activity, as described herein. Desired therapeutic effects also include, but are not limited to curing or healing the subject, alleviating, relieving, altering or ameliorating a disease or disorder in the subject or at least one symptom of said disease or disorder in the subject, or otherwise improving or affecting the health of the subject.

Ameliorating at least one symptom of the disease or disorder being treated in satisfactory although amelioration of several, if not all, symptoms of the disease or disorder is preferred.

A featured aspect of the invention pertains to methods of modulating the endoplasmic reticulum stress response pathway for therapeutic purposes.

Thus, the present invention features methods of treatment or therapeutic methods. In one aspect, the invention features a method of treating a subject (e.g., a human subject in need thereof) with a modulatory compound identified according to the present invention (e.g., an endoplasmic reticulum stress response pathway molecule modulator), such that a desired therapeutic effect is achieved.

In another aspect, the invention provides a method for preventing in a subject, a disease or condition associated with altered insulin sensitivity, e.g., obesity, diabetes, e.g., Type I or Type II, by administering to the subject an agent which modulates the expression or activity of the endoplasmic reticulum stress response pathway, e.g., BiP, ERO1, XBP-1 and CHOP1. Subjects at risk for such disorders can be identified, for example, using methods described herein or any one or a combination of diagnostic or prognostic assays known in the art. Administration of a prophylactic agent can occur prior to the manifestation of symptoms characteristic of the altered insulin sensitivity, such that a disease or disorder is prevented or, alternatively, delayed in its progression.

Depending on the type of insulin sensitivity aberrancy, for example, a compound that stimulates the expression and/or activity of an endoplasmic reticulum stress response pathway molecule or the expression and/or activity an endoplasmic reticulum stress response pathway-binding molecule, may be used for treating a subject. Agents for use can be known (e.g., sense or antisense nucleic acid molecules encoding an endoplasmic reticulum stress response pathway molecule or interacting molecules or the polypeptides they encode) or can be identified, e.g., using the screening assays described herein (e.g., a an endoplasmic reticulum stress response pathway molecule agonist or antagonist, a peptidomimetic of a an endoplasmic reticulum stress response pathway molecule agonist or antagonist, a an endoplasmic reticulum stress response pathway molecule peptidomimetic, or other small molecule).

Modulatory methods of the invention involve contacting a cell (e.g., an preadipocyte, adipocyte and/or a skeletal muscle cell) with a agent that modulates the activity and/or expression of an endoplasmic reticulum stress response pathway molecule and/or a an endoplasmic reticulum stress response pathway molecule interacting molecule.

These modulatory methods can be performed in vitro (e.g., by contacting the cell with the agent) or, alternatively, in vivo (e.g., by administering the agent to a subject). As such, the present invention provides methods of treating an individual afflicted with a condition or disorder that would benefit from up- or down-modulation of insulin sensitivity, e.g., a disorder characterized by an unwanted, insufficient, or aberrant insulin sensitivity. In one embodiment, the method involves administering an agent (e.g., an agent identified by a screening assay described herein), or combination of agents that modulates (e.g., upregulates or downregulates) the expression and/or activity of an endoplasmic reticulum stress response pathway molecule.

Subjects and Patients

In a preferred aspect, the invention features a method of treating a subject having an insulin response disorder, for example, altered insulin sensitivity or a weight disorder. The present invention also provides for therapeutic methods of treating a subject having pre-diabetes or symptoms thereof, hyperglycemia and/or Type I diabetes.

Identification or selection of a subject in need thereof can be accomplished by any skilled medical practitioner or researcher using art-recognized diagnostic skills or techniques. For example, a diabetic subject is a subject, e.g., a human subject, who has been diagnosed as having diabetes (or would be diagnosed as having diabetes) by a skilled medical practitioner or researcher. Preferred tests utilized in diabetes diagnosis include the fasting plasma glucose (FPG) test and the glucose tolerance test, e.g., the 75-g oral glucose tolerance test (OGTT). Exemplary criteria for the diagnosis of diabetes are set forth below.

| Normoglycemia | IFG or IGT‡ | Diabetes* |
|---|---|---|
| FPG < 110 mg/dl | FPG ≧ 110 and < 126 mg/dl (IFG) | FPG ≧ 126 mg/dl |
| 2-h PG† < 140 mg/dl | 2-h PG† ≧ 140 and < 200 mg/dl (IGT) | 2-h PG† ≧ 200 mg/dl |
| | | Symptoms of diabetes and casual plasma glucose concentration ≧ 200 mg/dl |

‡Midrange values indicating impaired glucose tolerance (IGT), or impaired fasting glucose (IFG).
*A diagnosis of diabetes must be confirmed, on a subsequent day, by measurement of FPG, 2-h PG, or random plasma glucose (if symptoms are present). Fasting is defined as no caloric intake for at least 8 h.
†This test requires the use of a glucose load containing the equivalent of 75 g anhydrous glucose dissolved in water. 2-h PG, 2-h postload glucose.

An insulin resistant subject is a subject, e.g., a human subject, who has been diagnosed as being insulin resistant (or would be diagnosed as being insulin resistant) by a skilled medical practitioner or researcher. An insulin resistant subject can be identified, for example, by determining fasting glucose and/or insulin levels in said subject. In a preferred embodiment, an insulin resistant subject has a fasting glucose level of less than 110 mg/dL and has a fasting insulin level of greater that 30 mU/L.

The effectiveness of treatment of a subject with a modulatory compound of the invention can be monitored by (i) detecting the level of insulin responsiveness or, alternatively, glucose tolerance in the subject prior to treating with the modulator; (ii) detecting the level of insulin responsiveness or, alternatively, glucose tolerance in the subject prior post treatment with the modulator; (iii) comparing the levels pre-administration and post administration; and (iv) altering the administration of the modulator to the subject accordingly. For example, increased administration of the modulator may be desirable if the subject continues to demonstrate insensitive insulin responsiveness.

Therapeutic Methods
Gene Therapy

In another aspect of the invention, a gene construct is used as a part of a gene therapy protocol to deliver a nucleic acid encoding an endoplasmic reticulum stress response pathway molecule protein, or a biologically active portion thereof.

Accordingly, the invention features expression vectors for in vivo or in vitro transfection and expression of an endoplasmic reticulum stress response pathway molecule (or a biologically active portion thereof) in particular cell types so as to increase the activity of at least one endoplasmic reticulum stress response pathway molecule in said cell. Such therapies are particularly useful where the naturally-occurring form of the protein is misexpressed or inappropriately activated. Expression constructs encoding an endoplasmic reticulum stress response pathway molecule (or a biologically active portion thereof) may be administered in any biologically effective carrier, e.g. any formulation or composition capable of effectively delivering the recombinant gene to cells in vivo. Approaches include insertion of the DNA encoding an endoplasmic reticulum stress response pathway molecule (or a biologically active portion thereof) in viral vectors including recombinant retroviruses, adenovirus, adeno-associated virus, and herpes simplex virus-1, or recombinant bacterial or eukaryotic plasmids. Viral vectors infect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $Ca_2PO4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that particular gene constructs provided for in vivo transduction of endoplasmic reticulum stress response pathway molecule expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding an endoplasmic reticulum stress response pathway molecule protein (or a biologically active portion thereof). Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller (1990) *Blood* 76:271). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079-9083; Julan et al. (1992) *J Gen Virol* 73:3251-3255; and Goud et al. (1983) *Virology* 163:251-254); or coupling cell surface receptor ligands to the viral env proteins (Neda et al. (1991) *J Biol Chem* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Moreover, use of retroviral gene delivery can be further enhanced by the use of tissue- or cell-specific transcriptional regulatory sequences that control expression of an endoplasmic reticulum stress response pathway molecule gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), adipocytes (Hertzel et al. (2000) *J Lipid Res.* 41:1082-1086), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in Methods in Molecular Biology, E. J. Murray, Ed. (Humana, Clifton, N.J., 1991) vol. 7. pp. 109-127). Expression of the inserted endoplasmic reticulum stress response pathway molecule gene can be under control of, for example, the E1A promoter, the major late promoter (MLP) and associated leader sequences, the E3 promoter, or exogenously added promoter sequences.

Yet another viral vector system useful for delivery of the DNA encoding an endoplasmic reticulum stress response pathway molecule (or a biologically active portion thereof) is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of an endoplasmic reticulum stress response pathway molecule (or a biologically active portion thereof) in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject endoplasmic reticulum stress response pathway molecule-encoding DNA by the targeted cell. Exemplary gene delivery systems of this type include liposomal derived systems, poly-lysine conjugates, and artificial viral envelopes.

In clinical settings, the gene delivery systems for therapeutic endoplasmic reticulum stress response pathway molecule administration can be introduced into a patient by any of a number of methods, each of which is familiar in the art. For instance, a pharmaceutical preparation of the gene delivery system can be introduced systemically, e.g. by intravenous injection. In this case, specific transduction of the protein in the target cells arises from specificity of transfection provided by the gene delivery vehicle, (i.e., cell-type or tissue-type specificity due to transcriptional regulatory sequences controlling recombinant gene expression). In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057). The DNA encoding an endoplasmic reticulum stress response pathway molecule (or a biologically active portion thereof), can be delivered in a gene therapy construct by electroporation using techniques described, for example, by Dev et al. ((1994) Cancer Treat Rev 20:105-115).

The present invention also includes therapeutic methods comprising injecting an area of a subject's body with an effective amount of a naked plasmid DNA compound (such as is taught, for example in Wolff et al., (1990) *Science* 247: 1465-1468). A naked plasmid DNA compound comprises a nucleic acid molecule encoding a TAP protein or biologically active portion thereof, operatively linked to a naked plasmid DNA vector capable of being taken up by and expressed in a recipient cell located in the body area. Preferred naked plasmid DNA vectors of the present invention include those known in the art. When administered to a subject, a naked plasmid DNA compound of the present invention transforms cells within the subject and directs the production of TAP protein, or biologically active portion thereof, in the cell.

A naked plasmid DNA compound of the present invention can be injected directly into fat and/or muscle cells or a subject in an amount such that the plasmid is taken up and expressed by the fat and/or muscle cells. As used herein, an effective amount of a naked plasmid DNA to administer to a subject comprises an amount needed to alleviate at least one symptom of the disease or disorder being treated and, preferably, is an amount sufficient to prevent or cure the disease or disorder. The mode of administration, number of doses and frequency of dose capable of being decided upon, in any given situation, by one of skill in the art without resorting to undue experimentation.

The present invention also includes therapeutic methods comprising administering to a subject a genetically-engineered human cell, for example, a genetically-engineered muscle cell or adipocyte, wherein the cell is engineered to overexpress an endoplasmic reticulum stress response pathway molecule gene. The terms "genetically-engineered cell" and "recombinant cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In one embodiment, a recombinant expression vector is introduced into the cell, the vector containing a nucleic acid molecule which encodes an endoplasmic reticulum stress response pathway molecule protein (or a biologically active portion thereof). As used herein, the term "vector" refers to a nucleic acid molecule capable of transporting another nucleic acid to which it has been linked. A preferred vector is an "expression vector" which is capable of directing the expression of gene contained therein. In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In a preferred embodiment, genetic engineering is of a subject or patient's own cells which are isolated from the subject or patient's body, transfected or infected according to the techniques described in detail herein, and reintroduced or returned to the body of the subject or patient.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like.

When using in mammalian cells, e.g., human cells, the expression vector's control functions are often provided by viral regulatory elements. For example, commonly used promoters are derived from polyoma, Adenovirus 2, cytomegalovirus and Simian Virus 40. Alternatively, tissue-specific regulatory elements are used to control expression of an endoplasmic reticulum stress response pathway molecule-encoding nucleic acid. Tissue-specific regulatory elements are known in the art. Preferred tissue-specific promoters include fat-specific promoters and muscle-specific promoters.

Vector DNA can be introduced via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the endoplasmic reticulum stress response pathway molecule protein or can be introduced on a separate vector. Cells stably transfected with the introduced nucleic acid can be identified by drug selection (e.g., cells that have incorporated the selectable marker gene will survive, while the other cells die).

Alternatively, the expression of an endogenous endoplasmic reticulum stress response pathway molecule gene can be modified, e.g., increased, within a cell by inserting a heterologous DNA regulatory element into the genome of the cell such that the inserted regulatory element is operatively linked with the endogenous endoplasmic reticulum stress response pathway molecule gene. For example, an endogenous endoplasmic reticulum stress response pathway molecule gene may be activated by inserting a regulatory element that is capable of promoting the expression of a normally expressed gene product in the cell. The heterologous regulatory element is inserted using techniques, such as targeted homologous recombination, which are well known to those of skill in the art, and described, e.g., in Chappel, U.S. Pat. No. 5,272,071; PCT publication No. WO 91/06667, published May 16, 1991.

Genetically-engineered cells are administered to a subject in need thereof, e.g., a subject having diabetes or an insulin-resistant subject, utilizing any art-recognized method for administering cells to a patient (see e.g., U.S. Pat. No. 5,538, 722). In a preferred embodiment, cells are administered via injection, for example, via injection into fat or muscle tissue of the subject in need of treatment.

The present invention also includes therapeutic methods comprising administering to a subject a therapeutically effective dose of an endoplasmic reticulum stress response pathway molecule protein or a biologically active portion thereof, such that endoplasmic reticulum stress response pathway molecule protein levels in said subject are increased or restored to levels detectable in normal or control (e.g., lean) individuals. Preferably, the endoplasmic reticulum stress response pathway molecule protein or biologically active portion thereof is made via recombinant means. Biologically active fragments (or portions) of endoplasmic reticulum stress response pathway molecules are produced by expression of a fragment (or portion) of an endoplasmic reticulum stress response pathway molecule-encoding nucleic acid molecule such that the endoplasmic reticulum stress response pathway molecule protein fragment (or portion) is produced recombinantly. Biologically active fragments (or portions) of an endoplasmic reticulum stress response pathway molecule can be produced by digestion of native or recombinantly produced endoplasmic reticulum stress response pathway molecule by, for example, using a protease, e.g., trypsin, thermolysin, chymotrypsin, or pepsin. Computer analysis (using commercially available software, e.g. MacVector, Omega, PCGene, Molecular Simulation, Inc.) can be used to identify proteolytic cleavage sites.

Recombinant proteins (or fragments) can be made according to any well-established methodology for expressing and purifying such proteins. For example, recombinant expression vectors can be designed for expression of endoplasmic reticulum stress response pathway molecule protein in prokaryotic or eukaryotic cells. For example, endoplasmic reticulum stress response pathway molecule protein can be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Recombinant expression vectors for expression of endoplasmic reticulum stress response pathway molecule protein in eukaryotic cells are described below. More routinely, however, recombinant endoplasmic reticulum stress response pathway molecule proteins are produced in prokaryotic cells, for example *E. coli* cells. Examples of suitable *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA modification and synthesis techniques, e.g., mutagenesis techniques.

In another embodiment, the endoplasmic reticulum stress response pathway molecule expression vector is a yeast expression vector. Examples of vectors for expression in yeast *S. cerevisiae* include pYepSec1 (Baldari, et al., (1987) *Embo J* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, endoplasmic reticulum stress response pathway molecule protein can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

A prokaryotic, yeast or insect cell (into which a recombinant expression vector encoding an endoplasmic reticulum stress response pathway molecule protein has been introduced) is then cultured in a suitable medium such that the endoplasmic reticulum stress response pathway molecule protein is produced and the endoplasmic reticulum stress response pathway molecule protein is then isolated or purified from the medium or the host cell. When the endoplasmic reticulum stress response pathway molecule protein or biologically active portion thereof is recombinantly produced, it is also preferably substantially free of culture medium, i.e., culture medium represents less than about 20%, more preferably less than about 10%, and most preferably less than about 5% of the volume of the protein preparation. In some instances it may be desirable to utilize a solubilizing agent such that the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Protein Therapy

The invention also provides for reduction of the endoplasmic reticulum stress response pathway molecule proteins to generate mimetics, e.g. peptide or non-peptide agents, which are able to function in a manner similar to naturally-occurring endoplasmic reticulum stress response pathway molecule yet have improved therapeutic properties as compared to naturally-occurring endoplasmic reticulum stress response pathway molecule. A mimetic can be obtained by, for example, screening libraries of natural and synthetic compounds as disclosed herein that are capable of functioning in a manner similar to naturally-occurring endoplasmic reticulum stress response pathway molecule. A mimetic can also be obtained by, for example, rational drug design.

Activating Antibodies

The present invention also includes therapeutic methods comprising administering to a subject a therapeutically effective dose of an endoplasmic reticulum stress response pathway molecule activating antibody or biologically active portion thereof, such that endoplasmic reticulum stress response pathway molecule biological activity in said subject is increased or restored to levels detectable in normal or control (e.g., lean) individuals. Preferred antibodies include monoclonal antibodies, including humanized, chimeric and human monoclonals or fragments thereof. To generate such antibodies, a proteolytic or synthetic endoplasmic reticulum stress response pathway molecule fragment (alone or linked to a suitable carrier or hapten) can be used to immunize a subject (e.g., a mammal including, but not limited to a rabbit, goat, mouse or other mammal). For example, the methods described in U.S. Pat. Nos. 5,422,110; 5,837,268; 5,708,155; 5,723,129; and 5,849,531, can be used and are incorporated herein by reference. The immunogenic preparation can further include an adjuvant, such as Freund's complete or incomplete adjuvant, or similar immunostimulatory agent. Immunization of a suitable subject with an immunogenic proteolytic or synthetic endoplasmic reticulum stress response pathway molecule fragment preparation induces a polyclonal anti-endoplasmic reticulum stress response pathway molecule antibody response. The anti-endoplasmic reticulum stress response pathway molecule antibody titer in the immunized subject can be monitored over time by standard techniques, such as with an enzyme linked immunosorbent assay (ELISA) using immobilized endoplasmic reticulum stress response pathway molecule. Subsequently, the sera from the immunized subjects can be tested for their TAP stimulatory activity using any of the bioassays described herein.

Alternatively, it is also possible to immunize subjects with plasmids expressing an endoplasmic reticulum stress response pathway molecule using DNA immunization technology, such as that disclosed in U.S. Pat. No. 5,795,872, Ricigliano et al., "DNA construct for immunization"(1998), and in U.S. Pat. No. 5,643,578, Robinson et al., "Immunization by inoculation of DNA transcription unit" (1997).

The antibody molecules directed against an endoplasmic reticulum stress response pathway molecule can be isolated from the mammal (e.g., from the blood) and further purified by well known techniques, such as protein A chromatography to obtain the IgG fraction. At an appropriate time after immunization, e.g., when the anti-TAP antibody titers are highest, antibody-producing cells can be obtained from the subject and used to prepare e.g., monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an endoplasmic reticulum stress response pathway molecule immunogen as described above, and the culture supernatants of the resulting hybridoma cells are screened to identify a hybridoma producing a monoclonal antibody that binds an endoplasmic reticulum stress response pathway molecule.

Any of the many well known protocols used for fusing lymphocytes and immortalized cell lines can be applied for the purpose of generating an anti-endoplasmic reticulum stress response pathway molecule monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind endoplasmic reticulum stress response pathway molecule, e.g., using a standard ELISA assay. The antibodies can then be tested for endoplasmic reticulum stress response pathway molecule stimulatory activity using, for example, the assays described herein.

In another embodiment, the method involves administering to an isolated tissue or cell line from the subject a modulatory compound identified according to the methodology described herein, such that a desired effect is achieved. In another embodiment, the method involves genetically-engineering a tissue or cell line, e.g., a tissue or cell line from a subject or patient, such that endoplasmic reticulum stress response pathway molecule expression or activity is activated. Tissue or cell lines treated ex vivo with a endoplasmic reticulum stress response pathway molecule activator or genetically-engineered in accordance with the methodologies of the present invention are preferably introduced into the subject or patient after ex vivo manipulation, such that a desired therapeutic effect is achieved.

Antisense Nucleic Acid Molecules

The present invention also includes therapeutic methods comprising administering to a subject a therapeutically effective dose of an endoplasmic reticulum stress response pathway molecule antisense nucleic acid molecule that is complementary to a gene encoding an endoplasmic reticulum stress response pathway molecule or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews— Trends in Genetics*, Vol. 1(1) 1986; Askari, F. K. and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences encoding endoplasmic reticulum stress response pathway molecules that are known in the art, antisense nucleic acids of the invention can be designed according to the rules of Watson and Crick base pairing. The antisense nucleic acid molecule can be complementary to the entire coding region of an endoplasmic reticulum stress response pathway molecule mRNA, but more preferably is an oligonucleotide which is antisense to only a portion of the coding or noncoding region of an endoplasmic reticulum stress response pathway molecule mRNA. For example, the antisense oligonucleotide can be complementary to the region surrounding the translation start site of an endoplasmic reticulum stress response pathway molecule mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides may be used. Examples of modified nucleotides which may be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a an endoplasmic reticulum stress response pathway molecule or an endoplasmic reticulum stress response pathway molecule-interacting molecule protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In another embodiment, an antisense nucleic acid of the invention is a compound that mediates RNAi. RNA interfering agents include, but are not limited to, nucleic acid molecules including RNA molecules which are homologous to the target gene or genomic sequence, e.g., an endoplasmic reticulum stress response pathway molecule, or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P.A. and Zamore, P.D. 287, 2431-2432 (2000); Zamore, P.D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585-591) may be used to catalytically cleave an endoplasmic reticulum stress response pathway molecule mRNA transcripts to thereby inhibit translation of an endoplasmic reticulum stress response pathway molecule mRNA. A ribozyme having specificity for a an endoplasmic reticulum stress response pathway molecule-encoding nucleic acid can be designed based upon the nucleotide sequence or another nucleic acid molecule encoding another an endoplasmic reticulum stress response pathway molecule polypeptide by one skilled in the art. For example, a derivative of a Tetrahymena L-19 IVS RNA can be constructed in which the nucleotide sequence of the active site is complementary to the nucleotide sequence to be cleaved in an endoplasmic reticulum stress response pathway molecule-encoding mRNA. See, e.g., Cech et al. U.S. Pat. No. 4,987,071; and Cech et al. U.S. Pat. No. 5,116,742. Alternatively, an endoplasmic reticulum stress response pathway molecule mRNA may be used to select a catalytic RNA having a specific ribonuclease activity from a pool of RNA molecules. See, e.g., Bartel, D. and Szostak, J. W., 1993, *Science* 261:1411-1418.

Alternatively, gene expression can be inhibited by targeting nucleotide sequences complementary to the regulatory region of an endoplasmic reticulum stress response pathway molecule (e.g., the an endoplasmic reticulum stress response pathway molecule promoter and/or enhancers) to form triple helical structures that prevent transcription of the an endoplasmic reticulum stress response pathway molecule gene in target cells. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In yet another embodiment, the an endoplasmic reticulum stress response pathway molecule nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., 1996, *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al., 1996, supra; Perry-O'Keefe et al., 1996, *Proc. Natl. Acad. Sci. USA* 93: 14670-675.

PNAs of an endoplasmic reticulum stress response pathway molecule nucleic acid molecules may be used in therapeutic and diagnostic applications. For example, PNAs may be used as antisense or antigene agents for sequence-specific modulation of gene expression by, for example, inducing transcription or translation arrest or inhibiting replication. PNAs of an endoplasmic reticulum stress response pathway molecule nucleic acid molecules can also be used in the analysis of single base pair mutations in a gene, (e.g., by PNA-directed PCR clamping; as 'artificial restriction enzymes' when used in combination with other enzymes, (e.g., S1 nucleases (Hyrup B., 1996, supra)); or as probes or primers for DNA sequencing or hybridization (Hyrup B. et al., 1996, supra; Perry-O'Keefe supra).

In another embodiment, PNAs of an endoplasmic reticulum stress response pathway molecule can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of an endoplasmic reticulum stress response pathway molecule nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B., 1996, supra). The synthesis of PNA-DNA chimeras can be performed as described in Hyrup B., 1996, supra and Finn P. J. et al., 1996, *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, may be used as a between the PNA and the 5' end of DNA (Mag, M. et al., 1989, *Nucleic Acid Res.* 17: 5973-88). PNA monomers are then coupled in a stepwise manner to produce a chimeric molecule with a 5' PNA segment and a 3' DNA segment (Finn P. J. et al., 1996, supra). Alternatively, chimeric molecules can be synthesized with a 5' DNA segment and a 3' PNA segment (Peterser, K. H. et al., 1975, *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. US.* 86:6553-6556; Lemaitre et al., 1987, *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., 1988, *Bio-Techniques* 6: 958-976) or intercalating agents. (See, e.g., Zon, 1988, *Pharm. Res.* 5:539-549). To this end, the oligonucleotide may be conjugated to another molecule, (e.g., a peptide, hybridization triggered cross-linking agent, transport agent, or hybridization-triggered cleavage agent).

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

The invention also provides for reduction of the expression and/or activity of an endoplasmic reticulum stress response pathway molecule in a cell utilizing an intracellular antibody specific for an endoplasmic reticulum stress response pathway molecule discussed herein. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T.M. et al. (1990) *FEBS Letters* 274:193-198; Carlson, J.R. (1993) *Proc. Natl. Acad Sci. USA* 90:7427-7428; Marasco, W.A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R.R. et al. (1994) *J. Biol. Chem.* 269:23931-23936; Beerli, R.R. et al. (1994) *Biochem. Biophys. Res. Commun.* 204:666-672; Mhashilkar, A.M. et al. (1995) *EMBO J.* 14:1542-1551; Richardson, J.H. et al. (1995) *Proc. Natl. Acad. Sci. USA* 92:3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101-108; Mhashilkar, A. M. et al. (1995) *EMBO J.* 14:1542-1551). A preferred nuclear localization signal to be used for nuclear targeting of the intracellular antibody chains is the nuclear localization signal of SV40 Large T antigen (see Biocca, S. et al. (1990) *EMBO J.* 9:101-108; Mhashilkar, A. M. et al. (1995) *EMBO J.* 14:1542-1551).

To prepare an intracellular antibody expression vector, antibody light and heavy chain cDNAs encoding antibody chains specific for the target protein of interest, e.g., an endoplasmic reticulum stress response pathway molecule protein, is isolated, typically from a hybridoma that secretes a monoclonal antibody specific for an endoplasmic reticulum stress response pathway molecule protein. For example, antibodies can be prepared by immunizing a suitable subject, (e.g., rabbit, goat, mouse or other mammal) with a an endoplasmic reticulum stress response pathway molecule protein immunogen. An appropriate immunogenic preparation can contain, for example, recombinantly expressed an endoplasmic reticulum stress response pathway molecule protein or a chemically synthesized an endoplasmic reticulum stress response pathway molecule peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a an endoplasmic reticulum stress response pathway molecule protein immunogen as described above, and the culture supernatants of the resulting hybridoma cells are screened to identify a hybridoma producing a monoclonal antibody that binds specifically to the an endoplasmic reticulum stress response pathway molecule protein. Any of the many well known protocols used for fusing lymphocytes and immortalized cell lines can be applied for the purpose of generating an anti-endoplasmic reticulum stress response pathway molecule protein monoclonal antibody (see, e.g., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal antibody that binds to an endoplasmic reticulum stress response pathway molecule can be identified and isolated by screening a recombinant combinatorial immunoglobulin library (e.g., an antibody phage display library) with the protein, or a peptide thereof, to thereby isolate immunoglobulin library members that bind specifically to the protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246: 1275-1281; Griffiths et al. (1993) *EMBO J.* 12: 725-734; Hawkins et al. (1992) *J Mol Biol* 226:889-896; Clarkson et al. (1991) *Nature* 352: 624-628; Gram et al. (1992) *PNAS* 89:3576-3580; Garrad et al. (1991) *Bio/Technology* 9: 1373-1377; Hoogenboom et al. (1991) *Nuc Acid Res* 19:4133-4137; Barbas et al. (1991) *PNAS* 88:7978-7982; and McCafferty et al. *Nature* (1990) 348:552-554.

Once a monoclonal antibody of interest specific for an endoplasmic reticulum stress response pathway molecule has been identified (e.g., either a hybridoma-derived monoclonal antibody or a recombinant antibody from a combinatorial library, including monoclonal antibodies to an endoplasmic reticulum stress response pathway molecule that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$)

and expressed as a single chain molecule. To inhibit transcription factor activity in a cell, the expression vector encoding the NIP45-specific intracellular antibody is introduced into the cell by standard transfection methods as described hereinbefore.

Peptidic Compounds

In another embodiment, an inhibitory compound of the invention is a peptidic compound derived from an endoplasmic reticulum stress response pathway molecule amino acid sequence. In particular, the inhibitory compound comprises a portion of an endoplasmic reticulum stress response pathway molecule (or a mimetic thereof) that mediates interaction of an endoplasmic reticulum stress response pathway molecule with a target molecule such that contact of the endoplasmic reticulum stress response pathway molecule with this peptidic compound competitively inhibits the interaction of the endoplasmic reticulum stress response pathway molecule with the target molecule.

The peptidic compounds of the invention can be made intracellularly in immune cells by introducing into the immune cells an expression vector encoding the peptide. Such expression vectors can be made by standard techniques. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

Other inhibitory agents that may be used to specifically inhibit the activity of an endoplasmic reticulum stress response pathway molecule protein are chemical compounds that directly inhibit endoplasmic reticulum stress response pathway molecule activity or inhibit the interaction between endoplasmic reticulum stress response pathway molecules and target molecules. Such compounds can be identified using screening assays that select for such compounds, as described in detail above.

Those skilled in the art will recognize, or be able to ascertain using no more than routine experimentation, many equivalents to the specific embodiments of the invention described herein. Where any concept(s) or element(s) of the invention is separately presented for convenience, it is understood that the combination of any such separately presented concept(s) or element(s), as necessary, is also encompassed by the invention. Such equivalents are intended to be encompassed by the claims.

The contents of the patents and references cited throughout this specification are hereby incorporated by reference in their entireties.

What is claimed:

1. A screening assay method for identifying a compound that decreases insulin resistance or increases insulin sensitivity, comprising
providing a cell-free composition that comprises a polypeptide which is an endoplasmic reticulum stress response pathway molecule;
contacting the cell-free composition with a test compound; and
determining an effect of the test compound on an activity of the polypeptide in the composition, wherein an increase in the activity of the polypeptide in the presence of the compound, relative to a suitable control, identifies the compound as one that decreases insulin resistance or increases insulin sensitivity wherein the polypeptide is selected from the group consisting of BiP, ERO-1, CHOP and XBP-1 and wherein said polypeptide has an effect on regulating glucose uptake which is in an insulin-dependent manner in the adipocyte or preadipocyte during adipogenesis.

2. The method of claim 1, wherein:
the polypeptide is an X box binding protein-1 (XBP-1) polypeptide, and wherein the composition further comprises a DNA molecule to which the XBP-1 polypeptide binds; and
wherein the effect of the test compound on activity of the XBP-1 polypeptide is determined by evaluating the binding of the XBP-1 polypeptide to the DNA molecule in the presence of the test compound.

3. The method of claim 1, wherein:
the polypeptide is a CCAAT/enhancer binding protein homologous protein (CHOP) polypeptide, and wherein the composition further comprises a target molecule to which the CHOP polypeptide binds; and
wherein the effect of the test compound on activity of the CHOP polypeptide is determined by evaluating the binding of the CHOP polypeptide to the target molecule in the presence of the test compound.

4. A method for identifying a compound that decreases insulin resistance or increases insulin sensitivity, comprising
providing a composition that comprises a polypeptide which is an endoplasmic reticulum stress response pathway molecule, wherein the composition is an adipocyte or preadipocyte cell which has been engineered to express the polypeptide by introducing into the adipocyte or preadipocyte an expression vector encoding the polypeptide;
contacting the composition with a test compound; and
determining an effect of the test compound on an activity of the polypeptide in the composition, wherein an increase in the activity of the polypeptide in the presence of the test compound, relative to a suitable control, identifies the compound as one that decreases insulin resistance or increases insulin sensitivity, wherein the polypeptide is selected from the group consisting of BiP, ERO-1, CHO-1 and XBP-1 wherein said activity is an effect of the polypeptide on regulating glucose uptake which is in an insulin-dependent manner in the adipocyte or preadipocyte during adipogenesis.

5. The method of claim 4, wherein the cell further comprises a reporter gene responsive to the activity of the polypeptide, and wherein the effect of the test compound on the activity of the polypeptide is determined by evaluating expression of the reporter gene in the presence of the test compound.

6. The method of claim 5, wherein:
the polypeptide is an X box binding protein-1 (XBP-1) polypeptide and wherein the reporter gene is responsive to the activity of the XBP-1 polypeptide; and
wherein the effect of the test compound on the activity of the XBP-1 polypeptide is determined by evaluating the expression of the reporter gene in the presence of the test compound.

7. The method of claim 5, wherein:
the polypeptide is an immunoglobulin heavy chain binding protein (BiP) polypeptide and the reporter gene is responsive to the activity of the BiP polypeptide; and
wherein the effect of the test compound on the activity of the BiP polypeptide is determined by evaluating the expression of the reporter gene in the presence of the test compound.

8. The method of any one of claims 6, 7, and 5, wherein the reporter gene is selected from the group consisting of: chloramphenicol acetyl transferase, luciferase, beta-galactosidase, firefly luciferase, alkaline phosphatase, human placental secreted alkaline phosphatase, and green fluorescent protein.

9. The method of claim 5, wherein:
the polypeptide is an X box binding protein-1 (XBP-1) polypeptide, and wherein the composition further comprises a target molecule to which the XBP-1 polypeptide binds; and
wherein the effect of the test compound on activity of the XBP-1 polypeptide is determined by evaluating the binding of the XBP-1 polypeptide to the target molecule in the presence of the test compound.

10. The method of claim 5, wherein:
the polypeptide is a CCAAT/enhancer binding protein homologous protein (CHOP) polypeptide, and wherein the composition further comprises a target molecule to which the CHOP polypeptide binds; and
wherein the effect of the test compound on activity of the CHOP polypeptide is determined by evaluating the binding of the CHOP polypeptide to the target molecule in the presence of the test compound.

* * * * *